(12) United States Patent
Bates et al.

(10) Patent No.: US 6,179,859 B1
(45) Date of Patent: Jan. 30, 2001

(54) EMBOLI FILTRATION SYSTEM AND METHODS OF USE

(75) Inventors: Mark C. Bates, Charleston, WV (US); Michael Horzewski, San Jose, CA (US)

(73) Assignee: Baff LLC, San Francisco, CA (US)

( * ) Notice: Under 35 U.S.C. 154(b), the term of this patent shall be extended for 0 days.

(21) Appl. No.: 09/354,897

(22) Filed: Jul. 16, 1999

(51) Int. Cl.$^7$ ................................................ A61F 2/01
(52) U.S. Cl. ................................ 606/200; 606/114
(58) Field of Search .................. 606/200, 127, 606/114

(56) References Cited

U.S. PATENT DOCUMENTS

| | | |
|---|---|---|
| 3,592,186 | 7/1971 | Oster . |
| 3,683,904 | 8/1972 | Forster . |
| 3,952,747 | 4/1976 | Kimmell, Jr. . |
| 3,996,938 | 12/1976 | Clark, III . |
| 4,046,150 | 9/1977 | Schwartz et al. . |
| 4,723,549 | 2/1988 | Wholey et al. . |
| 4,790,812 | 12/1988 | Hawkins, Jr. et al. ............. 604/22 |
| 4,921,484 | 5/1990 | Hillstead ........................... 604/104 |
| 4,969,891 | 11/1990 | Gewertz ........................... 606/200 |
| 4,998,539 | 3/1991 | Delsanti ........................... 128/898 |
| 5,002,560 | 3/1991 | Machold et al. .................. 606/198 |
| 5,011,488 | 4/1991 | Ginsburg .......................... 606/159 |
| 5,071,407 | 12/1991 | Termin et al. .................... 604/104 |
| 5,102,415 | 4/1992 | Guenther et al. ................. 606/159 |
| 5,108,419 | 4/1992 | Reger et al. ...................... 606/200 |
| 5,133,733 | 7/1992 | Rasmussen et al. .............. 606/200 |
| 5,190,555 | * 3/1993 | Wetter et al. ..................... 606/127 |
| 5,329,942 | 7/1994 | Gunther et al. .................. 128/898 |
| 5,354,310 | 10/1994 | Garnic et al. .................... 606/198 |
| 5,370,657 | 12/1994 | Irie .................................... 606/200 |
| 5,415,630 | 5/1995 | Gory et al. ........................ 604/53 |
| 5,456,667 | 10/1995 | Ham et al. ........................ 604/107 |
| 5,476,104 | 12/1995 | Sheahon ........................... 128/757 |
| 5,658,296 | 8/1997 | Bates et al. ...................... 606/127 |
| 5,662,671 | 9/1997 | Barbut et al. .................... 606/170 |
| 5,746,758 | 5/1998 | Nordgren et al. ................ 606/159 |
| 5,769,816 | 6/1998 | Barbut et al. .................... 604/96 |
| 5,779,716 | 7/1998 | Cano et al. ....................... 606/114 |
| 5,792,300 | 8/1998 | Inderbitzen et al. ............. 156/244.13 |
| 5,795,322 | 8/1998 | Boudewijn ....................... 604/22 |
| 5,814,064 | 9/1998 | Daniel et al. ..................... 606/200 |
| 5,817,102 | 10/1998 | Johnson et al. .................. 606/108 |
| 5,827,324 | 10/1998 | Cassell et al. .................... 606/200 |
| 5,833,644 | 11/1998 | Zadno-Azizi et al. ........... 604/52 |
| 5,833,650 | 11/1998 | Imran ............................... 604/52 |
| 5,846,260 | 12/1998 | Maahs ............................... 606/200 |
| 5,876,367 | 3/1999 | Kaganov et al. ................. 604/8 |
| 5,893,867 | 4/1999 | Bagaoisan et al. ............... 606/198 |
| 5,895,399 | 4/1999 | Barbut et al. .................... 606/159 |
| 5,954,745 | * 9/1999 | Gertler et al. .................... 606/200 |
| 5,976,172 | * 11/1999 | Homsma et al. ................. 606/200 |
| 6,001,118 | * 12/1999 | Daniel et al. ..................... 606/200 |
| 6,068,645 | * 5/2000 | Tu .................................... 606/200 |
| 6,086,577 | * 7/2000 | Ken et al. ......................... 606/200 |

FOREIGN PATENT DOCUMENTS

WO 98/39053  9/1998  (WO) .

* cited by examiner

*Primary Examiner*—Paul J. Hirsch
(74) *Attorney, Agent, or Firm*—Fish & Neave; Nicola A. Pisano (57) ABSTRACT

An emboli filtration apparatus is provided comprising a guide wire having a filter element captured thereon, so that the guide wire is free to rotate and translate while the filter element remains stationary. The apparatus allows for movement and rotation of the guide wire as devices are advanced over it to treat occlusive disease, substantially without dislodging the filter element.

26 Claims, 4 Drawing Sheets

EMBOLI FILTRATION SYSTEM AND METHODS OF USE

FIELD OF THE INVENTION

The present invention relates apparatus and methods for removing emboli from the blood stream that are generated during treatment of vascular disease, such as angioplasty, atherectomy or stenting. More particularly, an emboli filtration device and methods are provided having a captured filter that enables movement of a guidewire associated with the filter without displacing the filter.

BACKGROUND OF THE INVENTION

Atherosclerosis and other vascular occlusive diseases are becoming prevalent today in many developed countries. In such diseases, the flow areas of blood vessels become narrowed or occluded by the buildup of plaque on the walls of the vessels, leading to ischemia, and depending upon the location of the vessel, damage to the organ or limb. A number of surgical and percutaneous procedures have been developed for treating stenosis in the coronary arteries and carotid arteries, including endarterectomy, angioplasty, atherectomy and stenting.

One problem frequently encountered during such procedures is that pieces of plaque ("emboli") often are dislodged from the stenosis or the vessel wall. Such emboli may travel inner smaller diameter regions of the vasculature, blocking blood vessels and causing ischemic injury. This problem is especially severe where the emboli are permitted to travel into the coronary arteries and carotid arteries, and can result in infarction, stroke and even death.

Emboli filtration devices are known in which filter elements are deployed against the walls of a vessel distal to a stenosis. Such filters typically comprise a polymer or wire sac mounted on a distal region of a guide wire or angioplasty catheter, and permit blood to flow through the filter while trapping emboli. Once treatment of the stenosis is completed, the filter containing the captured emboli is contracted and withdrawn from the vessel.

For example, U.S. Pat. No. 5,814,064 to Daniel et al. describes an emboli capturing system having a radially expandable mesh filter disposed on the distal end of a guide wire. The filter is deployed distal to a region of stenosis, and any interventional devices, such as an angioplasty balloon or stent delivery system are advanced along the guide wire. The filter is designed to capture emboli generated during treatment of the stenosis while permitting blood to flow through the filter.

U.S. Pat. No. 4,723,549 to Wholey et al. describes an angioplasty catheter having a filter element disposed on its distal end. The filter is supported on a plurality of circumferential struts, and is expanded against the interior wall of a vessel, distal to a stenosis, by an inflation balloon. An angioplasty balloon is disposed on the catheter proximal of the filter for dilating the stenosis. The filter captures emboli dislodged during the dilatation procedure, and then is contracted and removed from the vessel with the angioplasty catheter.

A key disadvantage of previously known emboli filtration systems, such as described in the foregoing patents, is that the filters in those devices are fixedly attached to the guide wire or angioplasty catheter, respectively. If the catheter or guide wire is rotated, bumped or moved after the filter has been deployed, there is a substantial risk that filter will become temporarily dislodged or skewed, thereby permitting emboli to escape past the filter. Moreover, movement of the deployed filter against the vessel wall also may damage the endothelium, and/or dislodge emboli distal to the filter. Such motion is especially likely to occur when other devices such as an angioplasty balloon catheter are deployed along the guide wire after the filter is deployed, as in the Daniels et al. patent.

In view of these disadvantages it would be desirable to provide emboli filtration apparatus and methods having a filter element that remains stationary once deployed.

It also would be desirable to provide emboli filtration apparatus and methods having a filter that may be deployed along a guide wire, but is configured so that subsequent displacements or rotation of the guide wire will not dislodge the filter.

It further would be desirable to provide emboli filtration apparatus and methods that reduce the risk of emboli escaping from a filter element.

It still further would be desirable to provide emboli filtration apparatus and methods that reduce the risk of trauma to vessel endothelium resulting from movement transferred to the emboli filtration apparatus.

SUMMARY OF THE INVENTION

In view of the foregoing, it is an object of this invention to provide emboli filtration apparatus and methods having a filter element that remains stationary once deployed.

It is another object of the present invention to provide emboli filtration apparatus and methods having a filter that may be deployed along a guide wire, but is configured so that subsequent displacements or rotation of the guide wire will not dislodge the filter.

It is also an object of this invention to provide emboli filtration apparatus and methods that reduce the risk of emboli escaping from a filter element.

It is a further object of the present invention to provide emboli filtration apparatus and methods that reduce the risk of trauma to vessel endothelium resulting from movement transferred to the emboli filtration apparatus.

These and other objects of the present invention are accomplished by providing emboli filtration apparatus comprising a guide wire having a filter element captured thereon, so that the guide wire is free to rotate and translate while the filter element remains stationary. The apparatus thus allows for movement and rotation of the guide wire as devices are advanced over it to treat a stenosis, substantially without dislodging the filter element. Accordingly, the risk of permitting emboli to escape during temporary displacement or skewing of the filter element is reduced, as well as movement-induced trauma of the vessel endothelium.

In a preferred embodiment, the apparatus comprises a guide wire having a filter element captured for rotation and translation on a distal end thereof. The filter element preferably comprises a wire or polymer sac affixed to a plurality of self-expanding struts. The filter element has a contracted state, suitable for transluminal insertion disposed inside a retractable sheath, and a deployed state, wherein an outer perimeter of the filter element engages the walls of a vessel when the sheath is retracted proximally.

The filter element includes a proximal capture ring having a diameter which is larger than the diameter of the guide wire, but smaller than the diameter of the distal tip of the guide wire. The capture ring allows the guide wire to move freely with relative to the filter element over a limited range, so that movement or rotation of the guide wire does not cause the filter to move or to scrape against the walls of the vessel. When it is desired to retract the filter element, the guide wire is pulled proximally so that the distal tip of the guide wire engages the capture ring and pulls the filter element back into a sheath to its contracted state.

Optionally, the filter element may include a cylindrical sleeve that ensures that the filter forms an adequate seal against the walls of the vessel in the deployed state, thus preventing bypass flow around the filter. The sleeve also assists in orienting the axis of the filter element parallel to the axis of the vessel.

Methods of using the apparatus of the present invention to remove emboli during a surgical or percutaneous transluminal procedure also are provided.

BRIEF DESCRIPTION OF THE DRAWINGS

Further features of the invention, its nature and various advantages will be apparent from the accompanying drawings and the following detailed description of the preferred embodiments, in which.

DETAILED DESCRIPTION OF THE INVENTION

The present invention is directed to an emboli filtration system and methods that filter out emboli generated during surgical or percutaneous interventional procedures. In accordance with the principles of the present invention, a filter element is captured on a guide wire so that the guide wire is capable of rotation and translation, without disturbing the placement of the filter element. Because the filter element is captured on the guide wire, however, the filter element is readily removed by retracting the guide wire into a sheath.

Figure 1:
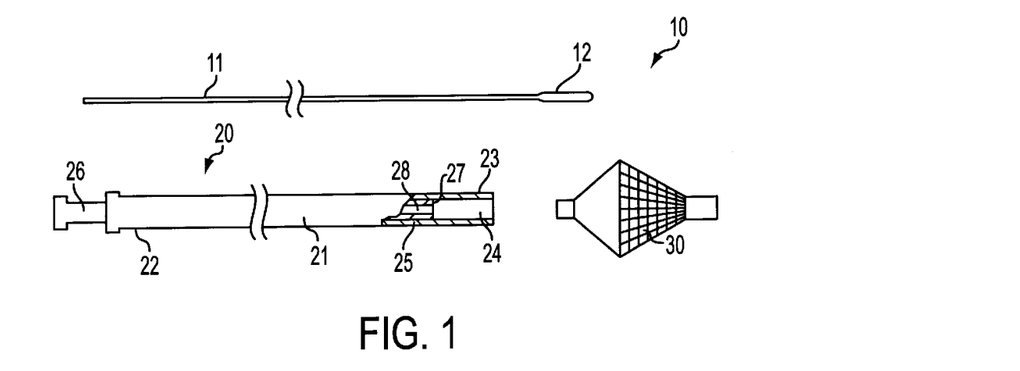
FIG. 1 is a side view of the components of a first embodiment of apparatus constructed in accordance with the principles of the present invention.

Referring to FIG. 1, apparatus 10 of the present invention comprises guide wire 11, delivery sheath 20 and filter element 30.

In accordance with the principles of the present invention, guide wire 11 includes enlarged diameter distal region 12. Guide wire 11 may be constructed of material commonly used in guide wire construction, such as stainless steel or a high strength polymer. Distal region 12, which acts as a stop to limit travel of filter element 30 in the distal direction, comprises a soft metal or metal alloy coil or may be formed from a flexible polymer, such as polyethylene or nylon, molded onto the distal region of the guide wire. Alternatively, guide wire 11 and distal region 12 may comprise a mechanism, such as are known in the art, for steering distal region 12 through a patient's vasculature. Illustratively, guide wire may have a diameter of 0.018 inches (0.46 mm) and the diameter of distal region 12 may be 0.022 inches (0.56 mm).

Delivery sheath 20 comprises flexible catheter 21 having proximal end 22, distal end 23, and interior lumen 24. Push tube 25 is disposed within lumen 24, and includes proximal end 26, distal end 27 and guide wire lumen 28, to permit catheter 21 and push tube 25 to be advanced along guide wire 11. Proximal end 26 of push tube 25 extends through proximal end 22 of catheter 21, so that push tube 25 may be translated in the distal and proximal directions relative to catheter 21. Catheter 21 and push tube 25 preferably comprise flexible materials such as are commonly used in catheter construction, for example, polyethylene, polyurethane or nylon. Delivery sheath 20 preferably has an outer diameter of about 4 Fr.

Figure 2A:
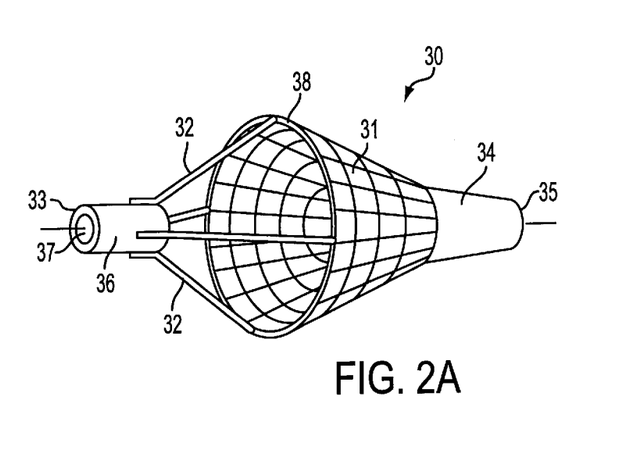
FIGS. 2A and 2B are, respectively, a perspective view and end view of the filter element of FIG. 1.
Figure 2B:
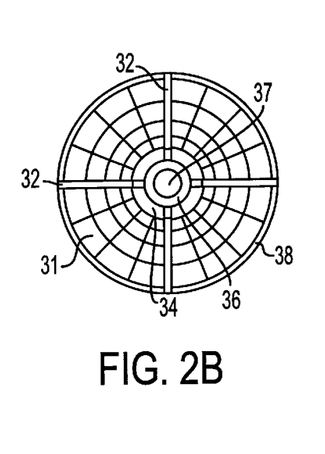

Referring now also to FIGS. 2A and 2B, filter element 30 comprises funnel-shaped filter sac 31 coupled to a plurality of self-expanding struts 32 at proximal end 33 and soft elastomer cone 34 at distal end 35. Struts 32 are affixed to capture ring 36, and self-expand from a contracted state, when filter element is disposed in lumen 24 of catheter 21, and a deployed state, when filter element is ejected from delivery sheath 20. In the deployed state, struts 32 extend outward to urge the perimeter of sac 31 into engagement with the walls of a vessel.

Struts 32 may comprise a resilient metal or metal alloy, such as stainless steel or nickel-titanium, or a resilient polymer. It is expected that at least three struts 32 spaced equidistant apart around the perimeter of sac 31 should be employed to provide adequate expansion and control of the sac, although a greater number may be used. Alternatively, struts 31 may comprise flexible strands, and expansion of sac 31 may be accomplished by adding a flexible and resilient self-expanding nickel-titanium hoop along perimeter 38 of the sac.

Particulate matter, such as emboli, pass through struts 32 and are trapped against sac 31, which permits blood to pass freely through. The size of emboli trapped by sac 31 is determined by the pore size of the sac, and preferably is about 0.0012 inches (30 microns). Sac 31 may comprise a polymer sleeve affixed to struts 32 or a self-expanding wire mesh constructed from a resilient metal alloy, for example, nickel-titanium.

Capture ring 36 has bore 37 with an inner diameter greater than the diameter of guide wire 11, but smaller than the diameter of distal region 12. This allows guide wire 11 to be rotated or translated distally relative to filter element 30, without imposing a force on the filter element that might temporarily dislodge the filter element. Accordingly, various devices, such as angioplasty catheters, atherectomy devices or stent delivery systems may be exchanged on guide wire 11 without disturbing filter element 30 or causing it to scrape against the walls of the vessel. As will of course be understood, capture ring 36 need not be a tubular member, but may have any suitable shape that allows guide wire 11 to pass freely through it.

Elastomer cone 34 is coupled to the distal end of sac 31 and includes a tapered central lumen that permits guide wire 11 to freely pass through cone 34 with minimal clearance. Elastomer cone 34 preferably comprises a non-stick or slick surface, such as polytetrafluoroethylene, and is designed so that emboli trapped in sac 31 are prevented from passing out of the filter element through the space between guide wire 11 and the lumen of elastomer cone 34. Cone 34 is sufficiently soft and flexible so that its lumen can expand to permit distal region 12 of guide wire 12 to be pulled proximally through the cone, and then the lumen will seal itself to prevent emboli from escaping through the lumen, as described hereinafter.

Figure 3A:
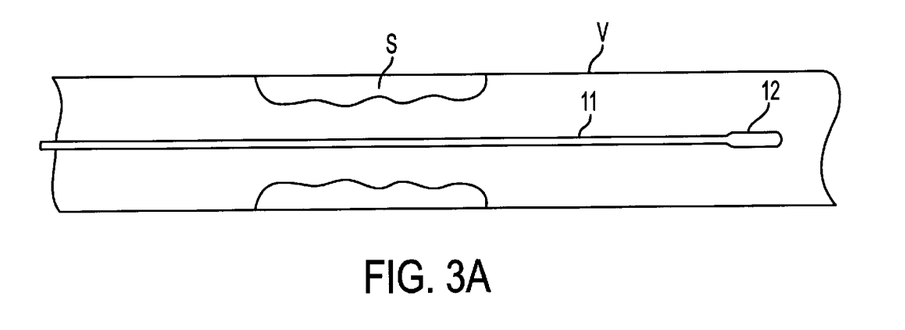
FIGS. 3A–3E are side sectional views showing deployment, use and removal of the apparatus of FIG. 1 in accordance with the methods of the present invention.

Referring now to FIGS. 3A to 3E, methods of using the apparatus of FIG. 1 is described. In FIG. 3A, guide wire 11 first is percutaneously and transluminally inserted into vessel V, such as a coronary artery or common carotid artery, so that distal region 12 is disposed distal to stenosis S in the direction of blood flow (indicated by arrow F).

Figure 3B:
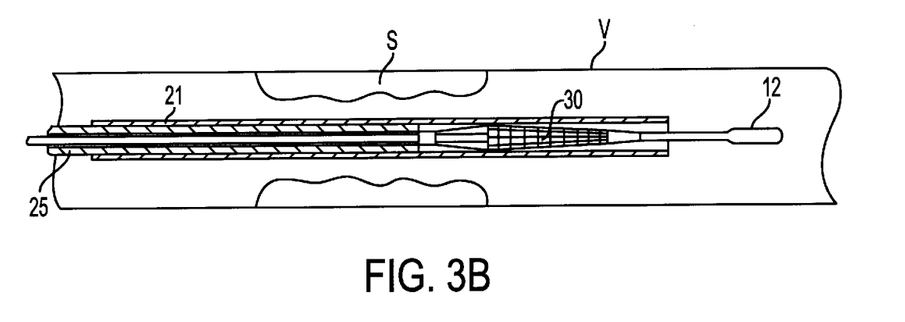

In FIG. 3B, delivery sheath 20 with filter element 30 loaded in lumen 24 in the contracted state is advanced along guide wire 11 until the filter element is disposed at a desired location distal to the stenosis, as determined, for example, by fluoroscopy. Proximal end 28 of push tube 25 is then held stationary while catheter 21 is retracted in the proximal direction.

Figure 3C:
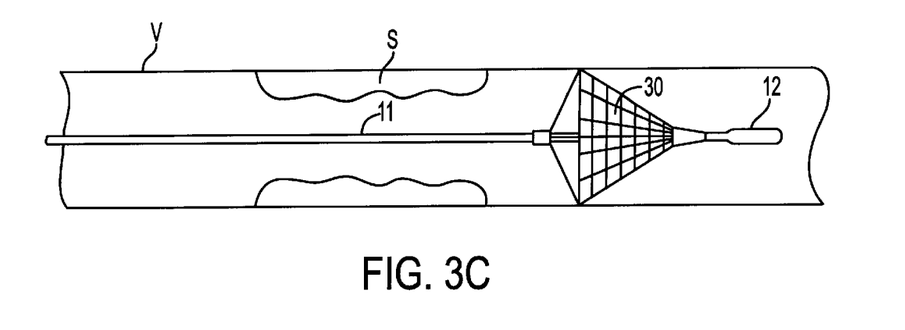

As catheter 21 is retracted, struts 32 of filter element 30 expand outward to urge the perimeter of sac 31 into engagement with the walls of vessel V, as depicted in FIG. 3C. Delivery sheath 20 is then withdrawn proximally and removed from guide wire 11. Guide wire 11 then may be advanced a short distal distally, so that any incidental movement of the guide wire associated with exchanging interventional instruments along guide wire 11 will not cause distal region 12 to contact filter element 30.

Figure 3D:
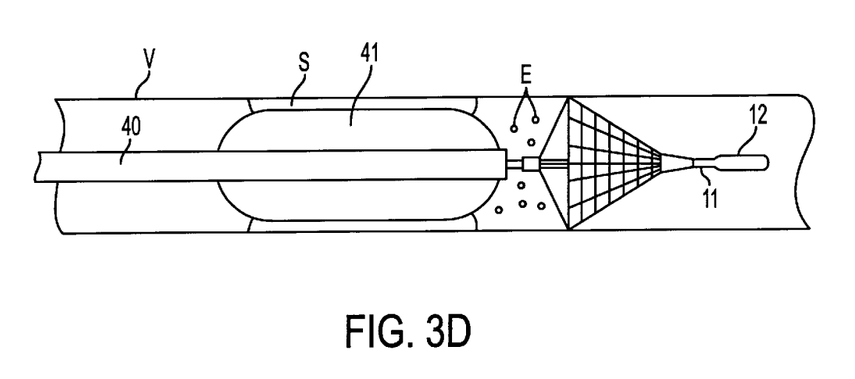

In FIG. 3D, angioplasty catheter 40 is illustratively advanced along guide wire 11 until balloon 41 is disposed across the stenosis. Balloon 41 then is inflated and deflated for one or several cycles, as in conventional, to dilate and disrupt the plaque comprising stenosis S and increase the diameter of vessel V. During this dilatation procedure, particles of plaque or emboli E are generated. These emboli are carried by blood flow in direction F into sac 31 of filter element 30, where they become trapped.

Insertion and advancement of angioplasty catheter 40 along guide wire 11 may cause the guide wire to be translated over a short range or rotated. Because filter element 30 is not affixed to guide wire 11, however, such motion of the guide wire is not transferred to the filter element. Instead, filter element 30 remains stationary even though the guide wire rotates or translates relative to the filter element.

Once balloon 41 has dilated stenosis S, angioplasty catheter 40 is withdrawn along guide wire 11 while leaving the guide wire in place. If desired, a stent delivery system (not shown) may be advanced along guide wire 11 and one or more stents deployed across the dilated stenosis to retain the patency of the dilated vessel.

Figure 3E:
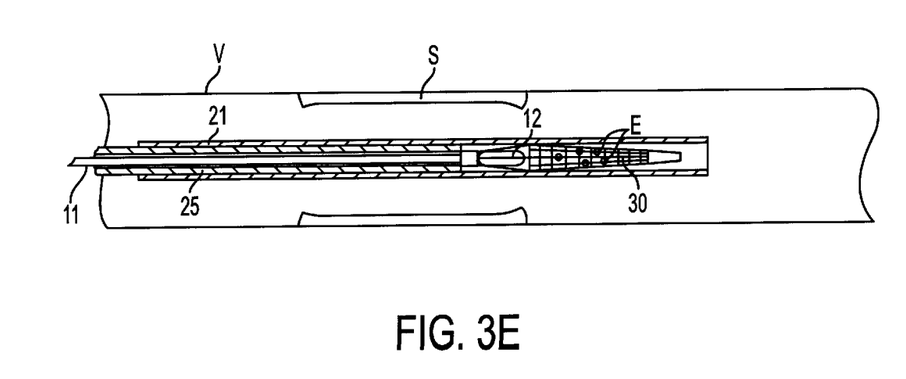

When treatment of the stenosis is completed, delivery sheath 20 (with push tube 25 removed) may again be advanced along guide wire 11 to a position just proximal of filter element 30. Guide wire 11 is then pulled proximally so that distal region passes through elastomer cone 34 and bears against capture ring 36. The lumen in cone 34 seals itself after distal region 12 passes through it so that emboli trapped in sac 31 do not escape through the lumen of cone 34.

When guide wire 11 is pulled further in the proximal direction, with catheter 21 held stationary, struts 32 are forced radially inward by distal edge of the catheter. This in turn causes sac 31 to disengage the vessel walls. As the guide wire continues to be pulled proximally, struts 32 cause sac 31 to collapse inward to its contracted position and the filter element is retracted into lumen 24 of catheter 21. Emboli E are trapped and retained in filter element 30 throughout treatment of the stenosis, and are withdrawn from the vessel when the filter element is retracted within catheter 21. Catheter 21 is then-removed from the vessel.

Figure 4A:
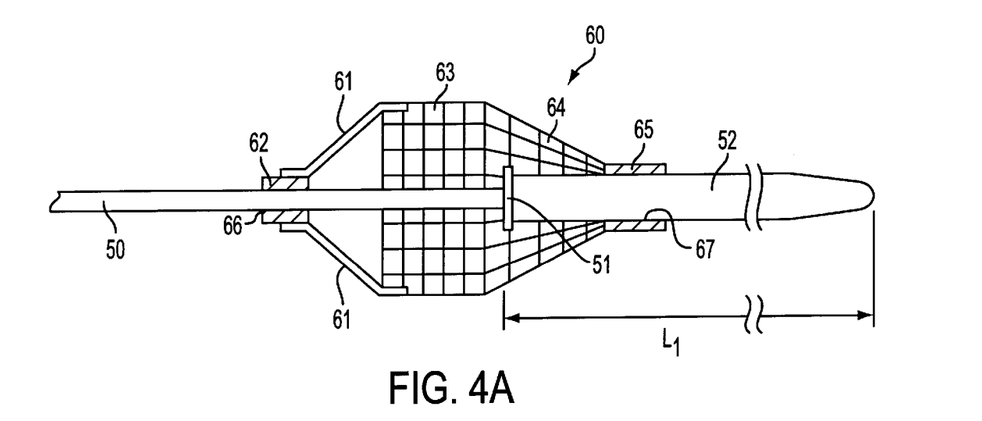
FIGS. 4A and 4B are, respectively, side sectional views of an alternative embodiment of the apparatus of the present invention in the deployed and contracted states.
Figure 4B:
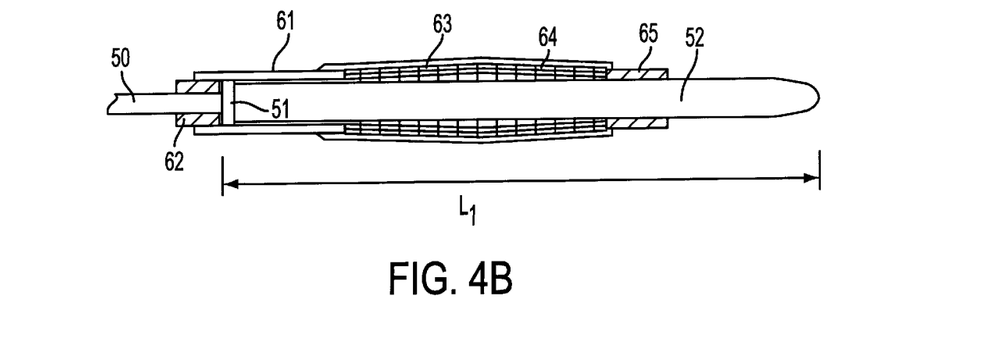

Referring now to FIGS. 4A and 4B, an alternative embodiment of the filter element and guide wire of the present invention is described. Guide wire 50 is similar in construction to guide wire 11 described with respect to FIG. 1, except that it includes flange 51 on enlarged diameter distal region 52 of guide wire 50, and enlarged distal region 52 has length $L_1$ that is longer than the length of the filter element 60 in the contracted state.

Distal region 52 may be formed from a malleable material, a coil spring, or a pliable thermoplastic material molded onto guide wire 50, and preferably is covered with a smooth hydrophillic coating to facilitate movement of filter element 60 as described hereinafter. Alternatively, guide wire 50 and distal region 52 may comprise a mechanism, such as are known in the art, for steering distal region 52 through a patient's vasculature. Distal region 52 also may comprise a radiopaque material or may include a radiopaque band 53 to assist in visualization and placement of the guide wire.

Filter element 60 comprises self-expanding struts 61 coupled to capture ring 62 and tubular sleeve 63. Sleeve 63 is affixed at its distal end to funnel-shaped filter sac 64, which in turn is coupled to distal ring 65. Capture ring 62 has bore 66 with an inner diameter larger than the diameter of guide wire 50, but smaller than the diameter of distal region 52. Accordingly, guide wire 50 may freely translate and rotate through bore 66 of capture ring 62 while the filter element remains stationary. Distal ring 65 has bore 67 with a diameter slightly larger than the diameter of distal region 52. This enables distal ring 65 to slide or rotate freely over distal region 52, but with minimal clearance for emboli to escape from sac 64 through the annulus between distal ring 65 and distal region 52. Distal region 52 includes flange 51, which has a diameter that is larger than the diameter of bore 66 of capture ring 62. Thus, filter element 60 is captured on guide wire 50 proximally by distal ring 65 abutting against flange 51, and distally by capture ring 62 abutting against flange 51.

Sleeve 63 and sac 64 filter blood passing through the vessel, and have a pore size selected to filter out particles having a diameter greater than 0.0012 inches (30 microns). Sleeve 63 and sac 64 preferably comprise a flexible woven metal alloy, polymer tube, or perforated fabric, and are expanded to the deployed state by struts 61. Advantageously, sleeve 63 is designed so that its perimeter conforms to the inner diameter of the vessel to seal against bypass flow, even in curved vessels. In addition, sleeve 63 tends to prevent skewing of the filter element and ensures that the filter is properly oriented parallel to the axis of the vessel when the filter element is deployed.

Filter element 60 is suitable for delivery percutaneously and transluminally to a desired location in a vessel using delivery sheath 20 of FIG. 1. In particular, struts 61 may be radially compressed to collapse sleeve 63 and sac 64, thereby permitting these the filter element to be loaded into lumen 24 of catheter 21 so that capture ring 62 abuts against distal end 27 of push tube 25.

Deployment of filter element 60 is similar to the method described with respect to FIGS. 3B and 3C. Specifically, delivery sheath 20 is advanced through a vessel with distal region 52 extending beyond distal end 23 of catheter 21. Once the distal region has crossed the stenosis, as confirmed by fluoroscopy, push tube 25 is held place and catheter 21 is retracted proximally. Alternatively, push tube 25 may be omitted and guide wire 50 may be held stationary with filter element 60 held in position by flange 51. Retraction of catheter 21 uncovers filter element 60, allowing struts 61 to expand outward and urge the perimeter of sleeve 63 and sac 64 into engagement with the walls of the vessel.

Delivery sheath 20 then is removed, and one of more interventional devices may be serially employed on guide wire 50. As for the embodiment of FIG. 1, motion imparted to the guide wire during exchange of instruments along the guide wire causes the guide wire to slide through filter element 60 without causing skewing or displacement of the filter element. Advantageously, this prevents emboli from escaping sac 64 or damage to the endothelium caused by scraping of the filter element.

Once treatment of the stenosis is completed, the treatment device (e.g., angioplasty catheter, etc.) is removed, and delivery sheath 20 is again advanced along guide wire 50. When distal end 23 of catheter 21 is disposed adjacent to capture ring 62, guide wire 50 is pulled proximally. As a result of this motion, distal region passes through filter element 60 until flange 51 abuts against capture ring 62. Further proximal movement of guide wire 50 causes struts 61 to be urged inward, collapsing sleeve 63 and sac 64 so that they can be drawn into lumen 24 of catheter 21.

Unlike the embodiment of FIG. 1, where the distal region passes through cone 34, length $L_1$ is sufficiently long so that distal ring 65 is still disposed over the enlarged diameter of distal region 51 when the filter element is in the contracted state. Accordingly, when filter element 60 is contracted for removal, emboli cannot escape through bore 67 of distal ring 65, since the bore continues to be substantially blocked by distal region 52 of guide wire 50. Delivery sheath 20, guide wire 50 and filter element 60 are then removed from the vessel with any emboli trapped within the contracted filter element.

In a preferred embodiment of the apparatus of FIGS. 4, guide wire 50 has a suitable length for transluminal percutaneous applications and a diameter in a range of 0.006 and 0.025 inches, and more preferably 0.012 inches. Distal region 52 of guide wire 50 has a diameter larger than the diameter of guide wire 50, and preferably in a range of 0.010 and 0.038 inches, more preferably 0.018 inches.

While filter element 60 may any length suitable for an intended application, in one preferred embodiment, filter element 60 has a deployed length of 3.5 cm and a maximum deployed diameter of 12 mm. For this embodiment, length $L_1$ of distal region 52 preferably is 5.0 cm. For a guide wire having a diameter of 0.012 inches and proximal ring and distal region having equal diameters of 0.018 inches, capture ring 62 preferably has an inner diameter of 0.014 inches and an outer diameter of 0.018 inches. In this case distal ring 65 preferably has an inner diameter of 0.0181 inches and an outer diameter of 0.024 inches.

One skilled in the art will appreciate that the present invention may be practiced by other than the described embodiments, which are presented for purposes of illustration and not limitation. It is intended that the present application cover such variations or modifications as may be apparent from the described embodiment as may fall within the scope of the appended claims.

What is claimed is:

1. Apparatus for filtering emboli from blood flowing through a vessel, the apparatus comprising:
   a guide wire having a distal region and a stop on the distal region;
   a capture ring disposed for translation on the guide wire, the stop limiting translation of the capture ring in a distal direction; and
   a filter sac connected to the capture ring.

2. The apparatus of claim 1 wherein, when the filter sac is deployed in the vessel, rotation or distal translation of the guide wire relative to the capture ring does not displace the filter sac, but retraction of the guide wire in a proximal direction causes the stop to abut against the capture ring.

3. The apparatus of claim 1 further comprising a plurality of self-expanding struts coupled between the filter sac and the capture ring.

4. The apparatus of claim 1 further comprising an elastomeric cone affixed to a distal portion of the filter sac.

5. The apparatus of claim 3 further comprising a cylindrical sleeve coupled between the plurality of self-expanding struts and the filter sac.

6. Apparatus for filtering emboli from blood flowing through a vessel, the apparatus comprising:
   a guide wire having a first portion having a first diameter and a distal region having a second diameter greater than the first diameter; and
   a filter element having a capture ring disposed for translation on the first portion, the capture ring having an aperture greater than the first diameter but smaller than the second diameter,
   wherein rotation or distal translation of the guide wire relative to the capture ring does not displace the filter element.

7. The apparatus of claim 6 wherein the filter element comprises an expandable sac.

8. The apparatus of claim 7 wherein the filter element further comprises a plurality of struts coupling the expandable sac to the capture ring.

9. The apparatus of claim 8 wherein the struts are self-expanding.

10. The apparatus of claim 7 wherein the filter element further comprises an elastomeric cone affixed to a distal portion of the expandable sac.

11. The apparatus of claim 6 wherein the guide wire further comprises a flange disposed on the distal region having a diameter larger than the diameter of the aperture in the capture ring.

12. The apparatus of claim 8 wherein the filter element further comprises a cylindrical sleeve coupled between the plurality of struts and the expandable sac.

13. The apparatus of claim 7 wherein the filter element further comprises a distal ring coupled to the expandable sac, the distal ring having a bore with a diameter greater than the second diameter.

14. The apparatus of claim 6 wherein the filter region has a contracted state suitable for transluminal delivery, and the distal region has a length that is greater than a length of the filter element in the contracted state.

15. The apparatus of claim 6 wherein the filter region has a contracted state suitable for transluminal delivery, the apparatus further comprising a flexible catheter having a lumen and a push tube disposed in the lumen, the push tube having a guide wire lumen for accepting the guide wire, and wherein the lumen is sized to accept the filter element in the contracted state.

16. Apparatus for filtering emboli during treatment of occlusive disease in a vessel, the apparatus comprising:
   a guide wire having a first diameter and a distal region having a second diameter greater than the first diameter;
   a filter element having a sac coupled to a capture ring, the capture ring having an aperture greater than the first diameter but smaller than the second diameter,
   wherein the filter element is disposed on the guide wire and the guide wire extends through the aperture with the distal region disposed distally of the capture ring, so that when the filter element is deployed in the vessel, rotation or distal translation of the guide wire does not displace the filter element, but retraction of the guide wire in a proximal direction causes the distal region to abut against the capture ring.

17. The apparatus of claim 16 wherein the filter element further comprises a plurality of self-expanding struts coupled between the sac and the capture ring.

18. The apparatus of claim 17 wherein the filter element further comprises an elastomeric cone affixed to a distal portion of the sac.

19. The apparatus of claim 16 wherein the filter element further comprises a cylindrical sleeve coupled between the plurality of self-expanding struts and the capture ring.

20. The apparatus of claim 16 wherein the filter element further comprises a distal ring coupled to the sac, the distal ring having a bore with a diameter greater than the second diameter.

21. A method of filtering emboli from blood flowing through a vessel, the method comprising:
providing a guide wire having a distal region including a stop, and a filter element having a capture ring disposed for translation on the guide wire proximal of the stop;
transluminally inserting the guide wire and filter element into a vessel;
deploying the filter element to engage a wall of the vessel, the filter element filtering emboli out of blood flowing through the vessel;
advancing a treatment device along the guide wire to treat a portion of the vessel proximal to the location of the filter element, rotation or distal translation of the guide wire relative to the filter element imparted by the treatment device not displacing the filter element.

22. The method of claim 21 further comprising a step of, after use of the treatment device is completed, pulling the guide wire proximally so that the stop engages the capture ring and causes the filter element to return to the contracted state.

23. The method of claim 21 further comprising:
providing a delivery sheath; and
compressing the filter element to a contracted state to insert the filter element within the delivery sheath.

24. The method of claim 21 wherein the filter element comprises an expandable sac, and deploying the filter element comprises expanding the expandable sac so that a perimeter of the expandable sac contacts the wall of the vessel.

25. The method of claim 24 wherein the filter element further comprises a cylindrical sleeve and deploying the filter element further comprises expanding the cylindrical sleeve against the wall of the vessel.

26. The method of claim 21 further comprising providing a catheter having a lumen, and pulling the guide wire proximally causes the filter element to become retracted within the lumen.

* * * * *

UNITED STATES PATENT AND TRADEMARK OFFICE
CERTIFICATE OF CORRECTION

PATENT NO.     : 6,179,859 B1  
DATED          : January 30, 2001  
INVENTOR(S)    : Mark C. Bates et al.

It is certified that error appears in the above-identified patent and that said Letters Patent is hereby corrected as shown below:

<u>Column 8,</u>  
Line 43, change "region" to -- element --.  
Line 47, change "region" to -- element --.

<u>Column 9,</u>  
Line 10, change "between" to -- to --.  
Line 11, change "struts and the capture ring." to -- struts. --

Signed and Sealed this

Ninth Day of April, 2002

*Attest:*

JAMES E. ROGAN  
*Attesting Officer*   *Director of the United States Patent and Trademark Office*

Disclaimer

6,179,859 — Mark C. Bates, Charleston, WV (US); Michael Horzewski, San Jose, CA (US). EMBOLI FILTRATION SYSTEM AND METHODS OF USE. Patent dated Jan. 30, 2001. Disclaimer file Jul. 21, 2005, by the assignee, Baff LLC.

Hereby enters this disclaimer to claims 1-26 of said Patent.

*(Official Gazette, October 11, 2005)*